United States Patent [19]

Morgan

[11] Patent Number: 4,806,673

[45] Date of Patent: Feb. 21, 1989

[54] PREPARATION OF CYANOALKYLPHENOLS FROM BISPHENOLS

[75] Inventor: Ted A. Morgan, Midland, Mich.

[73] Assignee: The Dow Chemical Company, Midland, Mich.

[21] Appl. No.: 940,302

[22] Filed: Dec. 10, 1986

[51] Int. Cl.$^4$ ............................................ C07C 121/52
[52] U.S. Cl. .................................................... 558/332
[58] Field of Search ............................... 558/332, 410

[56] References Cited

U.S. PATENT DOCUMENTS

| | | | |
|---|---|---|---|
| 3,886,283 | 5/1975 | Dory et al. ........................... | 558/388 |
| 4,388,250 | 6/1983 | Farber et al. ........................ | 558/350 |
| 4,405,528 | 9/1983 | Everly ................................... | 558/350 |
| 4,459,224 | 7/1984 | van Der Weerdt et al. ..... | 252/522 R |
| 4,483,800 | 11/1984 | Everly et al. ........................ | 558/350 |
| 4,485,051 | 11/1984 | Everly et al. ........................ | 558/350 |
| 4,487,722 | 12/1984 | Everly et al. ........................ | 558/350 |
| 4,536,343 | 8/1985 | Ramachandran ................... | 558/341 |

OTHER PUBLICATIONS

A. Jonsson, *Act. Chem. Scand.*, 8, 1203–10 (1954).

*Primary Examiner*—Anton H. Sutto
*Attorney, Agent, or Firm*—Paula Sanders Ruhr

[57] ABSTRACT

A process for preparing cyanoalkyphenols comprising contacting a bisphenol with cyanide ion at elevated temperatures under reaction conditions sufficient to produce the desired cyanoalkylphenol.

Compounds, e.g. 4-(1-cyano-1-methylethyl)phenol, produced via this method are useful as chemical intermediates in the preparation of polyurethanes, epoxy resins and pharmaceutical and agricultural products.

19 Claims, No Drawings

PREPARATION OF CYANOALKYLPHENOLS FROM BISPHENOLS

CROSS-REFERENCE TO RELATED APPLICATION

This application is related to copending application Ser. No. 911,848, filed on Sept. 26, 1986.

BACKGROUND OF THE INVENTION

This invention relates to processes for the preparation of cyanoalkylphenols.

Cyanoalkylphenols have numerous applications and are particularly useful as chemical intermediates in the preparation of polyurethanes, epoxy resins and pharmaceutical and agricultural products.

Methods are known for preparing cyanoalkylphenols. One process for the preparation of cyanoalkylphenols involves a complex multi-step synthesis whereby a dimethylbenzylhalide is converted to the cyanide, ring nitrated, hydrogenated, and then subjected to diazotization. See A. Johnsson, *Act. Chem. Scand* 8, 1203–10 (1954). The problem with this process is that it is a low-yielding, multi-step, time-consuming, and uneconomical route.

Another process for the preparation of cyanoalkylphenols is disclosed in U.S. Pat. No. 4,405,528. This is a process for the synthesis of 4-(α-alkyl-α-cyanomethyl)-2,6-disubstituted phenol by reacting a 2,6-disubstituted phenol with a Friedel-Crafts addition agent in the presence of a Friedel-Crafts catalyst such as aluminum chloride to form the corresponding 4-(α-alkyl-α-oxomethyl)-2,6-disubstituted phenol, reducing the 4-(α-alkyl-α-oxomethyl)-2,6-disubstituted phenol to form the corresponding 4-(α-alkyl-α-hydroxymethyl)-2,6-disubstituted phenol and thereafter reacting the 4-(α-alkyl-α-hydroxymethyl)-2,6-disubstituted phenol with an alkali metal cyanide or an alkaline earth metal cyanide to form the desired 4-(α-alkyl-α-cyanomethyl)-2,6-disubstituted phenol.

A process for the preparation of 4-(α-hydrocarbyl-α-cyanomethyl)-2,6-disubstituted phenols is disclosed in U.S. Pat. No. 4,483,800 wherein said cyanomethylphenol is prepared by reacting a disubstituted phenol with an aldehyde and an alkali metal cyanide or an alkaline earth metal cyanide in a suitable solvent.

What is needed is a versatile one-step process for utilizing inexpensive, readily available starting materials to produce cyanoalkylphenols.

SUMMARY OF THE INVENTION

The present invention is a process for the preparation of cyanoalkylphenols which avoids many of the problems associated with prior methods as well as provides greater versatility than the previous methods. The process of the present invention comprises bringing together a bisphenol and cyanide ion at elevated temperatures under reaction conditions sufficient to produce a cyanoalkylphenol wherein the cyanoalkyl group is ortho or para to the hydroxy moiety.

DETAILED DESCRIPTION OF ILLUSTRATIVE EMBODIMENTS

The bisphenols useful in the process of this invention comprise a divalent bridging moiety wherein both valencies reside on the same carbon and two hydroxyphenyl moieties which may be substituted with the proviso that the hydroxy moieties are ortho or para to the bridging moiety.

Preferred bisphenols useful in the process of this invention correspond to the following general formula:

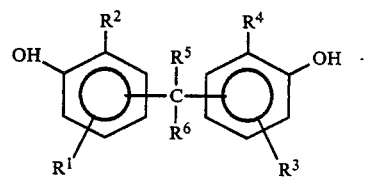

wherein $R^1$ and $R^3$ are independently in each occurrence ortho or para to the hydroxy moiety of the benzene ring to which they are bonded and the bridging unit between the two benzene rings is ortho or para to the hydroxy moieties of the benzene rings: $R^1$, $R^2$, $R^3$, and $R^4$ are independently hydrogen, $C_{1-20}$ straight or branched chain alkyl or $C_{3-10}$ carbocyclic, alkyl and carbocyclic in each instance being unsubstituted or substituted by one or more substituents selected from halo, e.g. chloro and bromo: alkyl, e.g., methyl, ethyl, propyl and others having up to 6 carbons: aryl, e.g., phenyl: alkoxy, e.g., methoxy; nitro; amino; sulfo; cyano: acyl and the like with the proviso that none of these interfere with the production of the cyanoalkylphenols of this invention; and $R^5$ and $R^6$ are independently hydrogen, $C_{1-20}$ straight or branched chain alkyl, or $R^5$ and $R^6$ may combine to form a $C_{3-20}$ carbocyclic, alkyl and carbocyclic in each instance being unsubstituted or substituted by one or more substituents selected from halo, e.g. chloro and bromo; alkyl, e.g., methyl, ethyl, propyl and others having up to 6 carbons: aryl, e.g., phenyl; alkoxy, e.g., methoxy; nitro; amino; sulfo; cyano; acyl and the like with the proviso that none of these interfere with the production of the cyanoalkylphenols of this invention.

In the preferred embodiments of this invention, $R^1$, $R^2$, $R^3$, and $R^4$, are each independently hydrogen or $C_{1-6}$ alkyl; $R^5$ and $R^6$ are each independently $C_{1-6}$ alkyl; $R^1$ and $R^3$ are each ortho to the hydroxy moiety and the bridging unit is para to each of the hydroxy moieties. In the more preferred form, $R^1$, $R^2$, $R^3$ and $R^4$ are each independently hydrogen or methyl and it is most preferred that $R^1$, $R^2$, $R^3$ and $R^4$ are each hydrogen and $R^5$ and $R^6$ are each methyl.

A preferred manner of practicing this invention constitutes heating a solventless mixture of Bisphenol A and cyanide ion in a closed vessel to about 185° C. and maintaining that temperature for about 20 hours to produce 4-(1-cyano-1-methylethyl)phenol. Preferred conversions and yields based on Bisphenol A are about 100 percent and 80 percent respectively.

Cyanide ion as used herein means a cyanide ion in salt form and specifically excludes hydrogen cyanide. Suitable forms of cyanide ion include lithium cyanide, tetraalkylammonium cyanide, sodium cyanide and potassium cyanide. Preferred forms of cyanide ion include sodium cyanide and potassium cyanide, with sodium cyanide being most preferred.

The process of this invention can be carried out using any molar ratio of cyanide ion to bisphenol that will provide sufficient cyanide ion to form the desired cyanoalkylphenol. A preferred molar ratio of cyanide ion to bisphenol is typically in the range of from about 1:1 to about 10:1, with about 1:1 to about 5 1 being more preferred. The most preferred molar ratio is about about 1:1.

The process of the present invention can be carried out at any temperature at which the reaction will proceed. Preferably, the reaction mixture is elevated to a temperature in the range from about 120° C. to about 200° C., with the range of about 150° C. to about 200° C. being more preferred. The most preferred temperature range is from about 180° C. to about 190° C.

The process is carried out for a period of time which will allow substantial conversion of the starting material. Preferred reaction times are in the range from about 10 to about 40 hours, with about 20 hours being most preferred. The process of the present invention can be carried out at any pressure at which the reaction will proceed up to about 20 psi (1.38×105 Pascals). The preferred pressure is that which is generated by the reactants themselves, i.e., autogeneous pressure, in a closed vessel.

The present process may be carried out neat or a solvent may be employed. Any solvent which is inert and will dissolve the starting materials can be employed in the present process. Aprotic solvents such as N,N-dimethylformamide, dimethylsulfoxide, formamide, glyme, diglyme, glycol, hexamethylphosphoramide, or N-methylpyrrolidone are preferred with N,N-dimethylformamide being the most preferred solvent. When solvent is employed, it is used in amounts sufficient to dissolve a sufficient amount of reactants to facilitate the reaction, preferably in amounts in the range from about 50 to about 75 weight percent based on the weight of the reaction medium. However, in the most preferred embodiment of this invention, no solvent is employed.

The product phenol is recovered by typical separation methods of distillation, extraction, filtration or recrystallization.

The reaction scheme can be represented by the following:

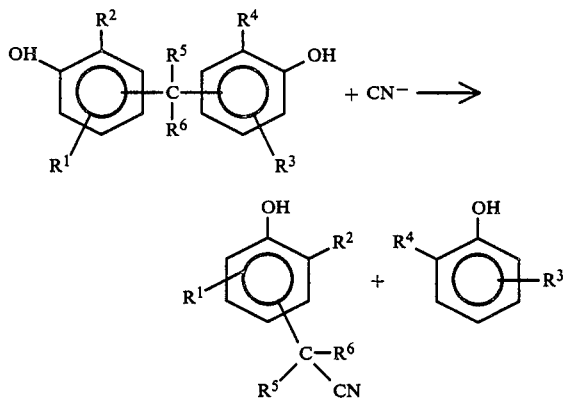

wherein $R^1$, $R^2$, $R^3$, $R^4$, $R^5$ and $R^6$ are as defined above.

Conversions typically obtained in the practice of the process of this invention are in the range from about 80 to 100 percent based on bisphenol. Preferred conversions are about 100 percent. Selectivities to the product cyanoalkylphenol obtained in the practice of this invention are in the range from about 70 to about 80 percent. Preferred selectivities are about 80 percent.

Typical cyanoalkylphenols readily prepared by the process of the present invention include 4-(1-cyano-1-methylethyl)phenol, 2-(1-cyano-1-methylethyl)phenol, 4-(2-(2-cyanobutyl))phenol, 2-(2-(2-cyanobutyl))phenol, 4-(2-(2-cyanopentyl))phenol, 2-(2-(2-cyanopentyl))phenol, 4-(3-(3-cyanopentyl))phenol, 2-(3-(3-cyanopentyl))phenol, 4-(2-(2-cyanohexyl))phenol, 2-(2-(2-cyanohexyl))phenol, 4-(3-(3-cyanohexyl))phenol, 2-(3-(3-cyanohexyl))phenol, 4-(1-(1-cyanocyclohexyl))phenol, 2-(1-(1-cyanocyclohexyl))phenol, 4-(1-(1-cyanocyclopentyl))phenol, 2-(1-(1-cyanocyclopentyl))phenol, 4-(1-(1-cyanocycloheptyl))phenol, and 2-(1-(1-cyanocycloheptyl))phenol, with 4-(1-cyano-1-methylethyl)phenol, 4-(2-(2-cyanobutyl))phenol, 4-(2-(2-cyanopentyl))phenol, 4-(3-(3-cyanopentyl))phenol, 4-(2-(2-cyanohexyl))phenol, 4-(3-(3-cyanohexyl))phenol, 4-(1-(1-cyanocyclohexyl))phenol, 4-(1-(1-cyanocyclopentyl))phenol, and 4-(1-(1-cyanocycloheptyl))phenol being preferred. The most preferred cyanoalkylphenol is 4-(1-cyano-1-methylethyl)phenol.

SPECIFIC EMBODIMENTS

The following example further illustrates the invention and should not be construed as limiting its scope. All parts and percentages are by weight unless otherwise indicated.

EXAMPLE 1

Preparation of 4-(1-Cyano-1-Methylethyl)Phenol

A 45.6 g portion (0.2 mol) of Bisphenol A and 10.7 g (0.22 mol) of sodium cyanide are heated at 185° C. for 20 hours in a 300 ml Parr stainless steel reactor equipped with a magnadrive stirrer. The reactor is opened and neutralized with aqueous HCL. The mixture is extracted three times with $CHCl_3$ using 300 ml each time. The combined layers from the $CHCl_3$ extractions are dried over MgSO4, filtered, and then concentrated to give a brown oil. The phenol is removed by vacuum distillation to give a brown solid pot residue. This crude residue is dissolved in $CHCl_3$, filtered through silica gel and then recrystallized from hot 1:1 $CHCl_3$-hexane to give 25.6 g of a colorless crystalline solid with a melting point of 99°–101° C. The product is characterized by nuclear magnetic resonance, gas chromatography, mass spectroscopy and infrared spectroscopy.

What is claimed is:

1. A process for the preparation of cyanoalkylphenol comprising bringing together a bisphenol and cyanide ion at elevated temperatures under reaction conditions sufficient to produce a cyanoalkylphenol wherein the cyanoalkyl group is ortho or para to the hydroxy moiety.

2. The process of claim 1 wherein the bisphenol corresponds to the following formula:

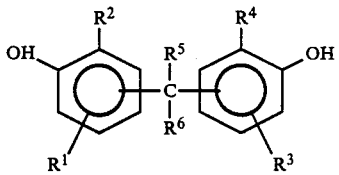

wherein
$R^1$ and $R^3$ are independently in each occurrence ortho or para to the hydroxy moiety of the benzene ring to which they are bonded and the bridging unit between the two benzene rings is ortho or para to the hydroxy moieties of the benzene rings;
$R^1$, $R^2$, $R^3$, and $R^4$ are independently hydrogen, $C_{1-20}$ straight or branched chain alkyl or $C_{3-10}$ carbocyclic, alkyl and carbocyclic in each instance being unsubstituted or substituted by one or more substituents selected from halo, alkyl, aryl, alkoxy, nitro, amino, sulfo, cyano, acyl and the like with the proviso that none of these interfere with the production of the cyanoalkylphenols of this invention; and $R^5$ and $R^6$ are independently hydrogen, $C_{1-20}$ straight or branched chain alkyl or $R^5$ and $R^6$ may combine to form a $C_{3-20}$ carbocyclic, alkyl and carbocyclic in each instance being unsubstituted or substituted by one or more substituents selected from halo, alkyl, aryl, alkoxy, nitro, amino, sulfo, cyano, acyl and the like with the proviso that none of these interfere with the production of the cyanoalkylphenols of this invention.

3. The process of claim 2 wherein $R^1$, $R^2$, $R^3$, and $R^4$ are each independently hydrogen or $C_{1-6}$ alkyl and $R^5$ and $R^6$ are each $C_{1-6}$ alkyl.

4. The process of claim 3 wherein $R^1$, $R^2$, $R^3$ and $R^4$ are each hydrogen and $R^5$ and $R^6$ are each methyl.

5. The process of claim 1 wherein the cyanide ion is in the form of sodium cyanide or potassium cyanide.

6. The process of claim 5 wherein the cyanide ion is in the form of sodium cyanide.

7. The process of claim 1 wherein the reaction takes place at a temperature in the range from about 120° C. to about 200° C.

8. The process of claim 7 wherein the reaction takes place at a temperature in the range from about 160° C. to about 200° C.

9. The process of claim 8 wherein the reaction takes place at a temperature in the range from about 180° C. to about 190° C.

10. The process of claim 9 wherein the reaction is allowed to proceed for a period of time in the range from about 10 to about 40 hours.

11. The process of claim 10 wherein the reaction is allowed to proceed for about 20 hours.

12. The process of claim 1 wherein no solvent is employed.

13. The process of claim 1 wherein the conversion based on bisphenol is between about 80 and 100 percent.

14. The process of claim 13 wherein the conversion based on bisphenol is about 100 percent.

15. The process of claim 14 wherein the selectivity to the product cyanoalkylphenol is about 80 percent.

16. The process of claim 4 wherein $R^1$ and $R^3$ are each ortho to the hydroxy moiety.

17. The process of claim 16 wherein the bridging unit is para to each of the hydroxy moieties.

18. A process wherein a solventless mixture of Bisphenol A and cyanide ion in the form of sodium cyanide is heated in a closed vessel to about 185° C. and maintained at that temperature for about 20 hours to produce 4-(1-cyano-1-methylethyl)phenol with a conversion of about 100 percent and a selectivity of about 80 percent based on Bisphenol A.

19. The process of claim 2 wherein the reaction is carried out at autogeneous pressure in a closed vessel.

* * * * *